US009795693B2

(12) United States Patent
Langereis et al.

(10) Patent No.: US 9,795,693 B2
(45) Date of Patent: Oct. 24, 2017

(54) DRUG CARRIER PROVIDING MRI CONTRAST ENHANCEMENT

(75) Inventors: Sander Langereis, Eindhoven (NL); Jochen Keupp, Rosengarten (DE); Holger Gruell, Eindhoven (NL); Dirk Burdinski, Eindhoven (NL); Danielle Beelen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1272 days.

(21) Appl. No.: 13/062,550

(22) PCT Filed: Sep. 3, 2009

(86) PCT No.: PCT/IB2009/053836
§ 371 (c)(1),
(2), (4) Date: Mar. 7, 2011

(87) PCT Pub. No.: WO2010/029469
PCT Pub. Date: Mar. 18, 2010

(65) Prior Publication Data
US 2011/0177009 A1 Jul. 21, 2011

(30) Foreign Application Priority Data
Sep. 10, 2008 (EP) .................................... 08164091

(51) Int. Cl.
| A61K 49/00 | (2006.01) |
| A61K 49/08 | (2006.01) |
| A61K 41/00 | (2006.01) |
| A61K 49/10 | (2006.01) |
| A61K 49/12 | (2006.01) |
| A61K 49/18 | (2006.01) |
| A61K 9/127 | (2006.01) |

(52) U.S. Cl.
CPC .............. *A61K 49/08* (2013.01); *A61K 9/127* (2013.01); *A61K 9/1271* (2013.01); *A61K 41/0028* (2013.01); *A61K 49/10* (2013.01); *A61K 49/12* (2013.01); *A61K 49/1812* (2013.01); *A61K 9/1273* (2013.01)

(58) Field of Classification Search
USPC ......................................................... 424/9.1
See application file for complete search history.

(56) References Cited

U.S. PATENT DOCUMENTS

| 6,088,613 | A | * | 7/2000 | Unger .............................. 600/420 |
| 7,635,722 | B1 | * | 12/2009 | Bachynsky et al. .......... 514/728 |
| 8,463,358 | B2 | | 6/2013 | Lamerichs et al. |
| 2003/0185760 | A1 | | 10/2003 | Lanza et al. |
| 2005/0136002 | A1 | | 6/2005 | Fossheim et al. |
| 2007/0237721 | A1 | | 10/2007 | Lanza et al. |
| 2011/0177009 | A1 | | 7/2011 | Langereis et al. |

FOREIGN PATENT DOCUMENTS

| EP | 1985312 A1 | 10/2008 |
| WO | 2006032705 A2 | 3/2006 |
| WO | 2006032705 A3 | 3/2006 |
| WO | 2007141767 A2 | 12/2007 |

OTHER PUBLICATIONS

Terreno et al. (Angew. Chem. Int. Ed. 2007, 46, 966-968).*
Kimura et al. (Mag. Reson. Imag. 2004, 22, 855-860).*
Dunand et al. (J. Am. Chem. Soc. 2000, 122, 1506-1512).*
Keupp et al. (Proc. Intl. Soc. Mag. Reson. Med. 2006, 14, 913).*
By J.C.Ross et al.; Registration and Integraton for Fluoroscopy Device Enhancement GE Research Center, Niskayuna NY 112309, USA; Case Western Reserve University, Cleveland, OH 44106, USA; J. Duncan and G. Gerig (Eds): MICCAI 2005, LNCS 3749 pp. 851-858.
By G.M. Lanza et al.; "Targeted Antiproliferative Drug to Vascular Smooth Muscle Cells With a Magnetic Resonance Imaging Nanoparticle Contrast Agent"; Implications for Rational Therapy of Restenosis; Received May 1, 2002; revision received Aug. 22, 2002; accepted Aug. 24, 2002.From the Department of Medicine, Division of Cardiology, Washington University Medical School, St. Louis, Mo (G.M.L., X.Y., P.M.W., D.R.A., M.J.S., L.K.C., R.W.F., D.E.S., S.A.W.), and the Department of Chemistry, Harvey Mudd College, Claremont, Calif (K.K.K.). Correspondence to Gregory M. Lanza, MD, PhD, Division of Cardiology, Washington University, 660 S Euclid Blvd—Campus Box 8086, St. Louis, MO 63110.
By A. M. Morawski et al; "Quantitative "Magnetic Resonance Immunohistochemistry" With Ligand-Targeted 19F Nanoparticles" Cardiovascular MR Latjoratories, Department of Medicine and Department of Biomedical Engineering, Washington University, Saint Louis, Missouri. Analytical Ctiemistry Group, University of Missouri Research Reactor, Columbia. Missouri. St. Thomas' Hospital, London, UK. Grant sponsor: National Institutes of Health; Grant numbers: HL-42950, HL-59865, EB-017(M, and NO1-CO-07121; Grant sponsor: Magnetic Resoance in Medicine 52: 1255-1263 (2004) Grant Sponsor: American Heart association; Grant Sponsor: Philips Medical Systems.

* cited by examiner

*Primary Examiner* — Michael G Hartley
*Assistant Examiner* — Melissa Perreira (57) ABSTRACT

Described are drug carriers useful in magnetic resonance imaging (MRI)-guided drug release comprising a shell capable of releasing an enclosed biologically active agent as a result of a local stimulus, e.g. energy input, such as heat, wherein the shell encloses a $^{19}$F MR contrast agent. Preferably, the carrier also acts as a contrast enhancement agent for MRI based on the principle of Chemical Exchange-dependent Saturation Transfer (CEST). To this end the shell encloses a cavity that comprises a paramagnetic chemical shift reagent, a pool of proton analytes, and the $^{19}$F contrast agent, and wherein the shell allows diffusion of the proton analytes.

19 Claims, 8 Drawing Sheets

Page: 1

DRUG CARRIER PROVIDING MRI CONTRAST ENHANCEMENT

FIELD OF THE INVENTION

The invention relates to Magnetic Resonance Imaging (MRI). Particularly, the invention pertains to the use of MRI and $^{19}$F MRI in the monitored or guided delivery of bio-active agents such as therapeutic or diagnostic agents (hereinafter referred to as "drugs"). More particularly, the invention relates to drug carriers to be used as MRI contrast agents in such monitored or guided delivery.

BACKGROUND OF THE INVENTION

Many diseases that are mostly localized in a certain tissue are treated with systemically administered drugs. A well-known example of standard cancer therapy is a systemic chemotherapy coming along with significant side effects for the patient due to undesired biodistribution and toxicity. The therapeutic window of these drugs is usually defined by the minimal required therapeutic concentration in the diseased tissue on the one hand, and the toxic effects in non-targeted organs, e.g. liver, spleen, on the other. Localized treatment by, for example, local release of cytostatics from nanocarriers promises a more efficient treatment and a larger therapeutic window compared to standard therapeutics. Localized drug delivery is also important if other therapeutic options such as surgery are too risky as is often the case for liver cancers. Localized drug delivery can also become the preferred treatment option for many indications in cardiovascular disease (CVD), such as atherosclerosis in the coronary arteries.

Magnetic Resonance Imaging, usually based on $^1$H as the magnetic nucleus, is an important diagnostic technique that is commonly used in hospitals for the diagnosis of disease. MRI allows for the non-invasive imaging of soft tissue with a superb spatial resolution.

Magnetic Resonance Imaging based on $^{19}$F instead of $^1$H opens up new diagnostic possibilities. The $^{19}$F nucleus has a high gyromagnetic ratio (40 MHz/T) and a natural isotopic abundance ratio of 100%. In the human body, $^{19}$F containing structures are exclusively present in the form of solid salts in e.g. teeth and bones. As a consequence, the $T_2$ relaxation times of the endogenous $^{19}$F atoms are extremely short and the MR signal is hardly detectable. In other words, the lack of endogenous $^{19}$F-based structures with relatively high transverse relaxation times assures a very low background MR signal. Therefore, exogenous $^{19}$F-based MRI contrast agents allow for "hot spot" imaging in a way similar to other techniques such as PET (positron emission tomography).

As a useful extension of its diagnostic use, MRI is also proposed for the monitoring of the delivery of bio-active agents such as therapeutic or diagnostic agents. I.e., MRI can not only be used for treatment planning, but also to control local drug delivery under image guidance.

In view of the aforementioned high specificity, it would be desired to employ $^{19}$F MRI not only as a diagnostic tool, but also in the MRI-assisted delivery of drugs or other biologically active agents. The same high specificity, however, also forms a practical barrier to the optimal use of $^{19}$F MRI herein. For, on the one hand, the addition of a $^{19}$F contrast agent to a drug carrier would mean that such a drug carrier were capable of being located by means of $^{19}$F MRI anytime, in view of the absence of natural $^{19}$F signal sources. On the other hand, it will mean that the detection of the $^{19}$F contrast agent does not provide information on the release of the biologically active agent, only on the presence of the contrast agent.

A reference respect of MRI monitored drug release is Ponce et al., J Natl Cancer Inst 2007; 99: 53-63. Herein a drug, doxorubicin, is taken up in a temperature-sensitive liposome. At body temperature, the doxorubicin remains in the inside of the liposome, whereas at a temperature of 41-42° C. the cytostatic drug is released from the inner aqueous compartment of the liposome. Thus, drug release can be facilitated by applying heat, as this will result in the opening-up of the liposome, whereupon drug release is no longer determined by diffusion (if any) through the liposomal shell. In order to monitor drug release by MRI, manganese is added to the formulation as an MRI contrast agent.

Almost all current MRI scans are based on the imaging of bulk water molecules, which are present at a very high concentration throughout the whole body in all tissues. If the contrast between different tissues is insufficient to obtain clinical information, MRI contrast agents (CAs), such as low molecular weight complexes of gadolinium, are administered. These paramagnetic complexes reduce the longitudinal ($T_1$) and transverse relaxation times ($T_2$) of the protons of water molecules. Also manganese acts as a $T_1$ contrast agent.

The manganese contrast agent in the aforementioned drug carrier will act upon its exposure to the bulk water molecules detected by MRI, i.e. it will lead to instantaneous MRI contrast enhancement upon opening up of the liposomal shell above the melt transition temperature of the lipids, after the application of heat.

As described, the MRI used in this drug release process is in fact used to monitor the actual release, so as to confirm that the thermo-sensitive liposomes actually work. I.e., it merely provides ex post facto information.

It would be advantageous to use $^{19}$F MRI to guide and/or monitor the local release of a biologically active agent such as a drug. It would also be advantageous to monitor the fate of a drug carrier as of its administration. Also, rather than confirming, instantaneously, the fact that the drug is released, such monitoring is desired as to determine in advance if, when and where the drug release should take place. Particularly with thermo-sensitive drug carriers, it would be advantageous to localize the drug carrier, and apply the heat that serves to facilitate drug release on the spot where desired, and at the moment in time when desired. It is further desired to provide a monitoring possibility that does not necessarily vanish with the process of releasing a drug, and that can preferably be used to quantify the drug release process and to evaluate therapeutic efficacy.

SUMMARY OF THE INVENTION

In order to better address the aforementioned desires, the invention, in one aspect, presents a carrier suitable for localized delivery of a biologically active agent, such as a drug, the carrier comprising a shell capable of releasing an enclosed biologically active agent, the drug, as a result of a local stimulus, e.g. energy input such as heat, wherein the shell encloses a $^{19}$F MR contrast agent.

In another aspect, the invention provides a combination of $^{19}$F MRI and $^1$H CEST MRI, and provides a carrier suitable for localized delivery of a biologically active agent, such as a drug, the carrier comprising a shell capable of releasing an enclosed biologically active agent the drug as a result of as a result of a local stimulus, e.g. energy input such as heat, wherein the shell encloses a chemical shift agent for lipo-CEST for $^1H$ MRI and a $^{19}F$ MRI contrast agent.

In another aspect, the invention provides a carrier suitable for the localized delivery of a biologically active agent, such as a drug, comprising contrast agents for both $^{19}F$ and $^1H$ MRI. Particularly, in a further aspect, the $^1H$ MRI contrast agent is selected from the group consisting of a $T_1$ and/or $T_2$ enhancement contrast agent, a CEST MR contrast agent, and a combination thereof.

In a further aspect, the invention provides a drug carrier comprising a thermosensitive, semipermeable shell enclosing a cavity, wherein the cavity comprises a $^{19}F$ contrast agent, a paramagnetic chemical shift reagent, and a pool of proton analytes, and wherein the shell allows diffusion of the proton analytes.

In yet another aspect, the invention provides a carrier for the controlled localized release of a bio-active agent, such as a therapeutic or diagnostic agent, comprising a thermosensitive, semipermeable shell enclosing a cavity, wherein the cavity comprises a $^{19}F$ contrast agent, a paramagnetic chemical shift reagent, and a pool of proton analytes, wherein the shell allows diffusion of the proton analytes, and wherein the shell can be modulated by heat so as to facilitate release of a bio-active agent comprised in the carrier.

BRIEF DESCRIPTION OF THE DRAWINGS

The invention will be illustrated with reference to the following, non-limiting examples and the accompanying non-limiting Figures.

DETAILED DESCRIPTION OF THE EMBODIMENT

In a broad sense, the invention can be described with reference to a carrier suitable for the localized delivery of a biologically active agent, such as a drug, comprising a $^{19}F$ contrast agent. The $^{19}F$ contrast agent undergoes a change in detectability upon its release from the carrier. Particularly, in the state wherein the $^{19}F$ agent is encapsulated in the carrier, the $^{19}F$ MR signal of the contrast agent is spectrally very broad. The $^{19}F$ contrast agent is thus hardly detectable. Upon release, however, the $^{19}F$ contrast agent becomes detectable, and yields a clear, preferably sharp signal in $^{19}F$ magnetic resonance.

Particularly, the invention can be described with reference to a carrier suitable for the localized delivery of a biologically active agent, such as a drug, comprising both a $^{19}F$ contrast agent and a CEST contrast agent.

The suitability of the carrier for the localized delivery of a biologically active agent, such as a drug (hereinafter referred to in short as "drug delivery") can refer to a variety of ways in which a carrier when loaded with a drug can be triggered to release the drug locally, e.g. by applying a controlled external force or delivering a sufficient amount of energy. This refers, e.g. to thermosensitive drug carriers that can be triggered to locally release a drug by applying local heat. Other methods for localized delivery do not necessarily involve thermosensitive carriers, but carriers that can be triggered to release a drug by a method of activation governed by properties other than thermosensitivity, including but not limited to pH, the presence of a gaseous core and/or layers, and sensitivity to externally applied ultrasound frequency/wavelength and intensity.

$^{19}F$ MRI Contrast Agents

With reference to the explanation given above, it will be clear that MR detectable $^{19}F$ does not naturally occur in the body and that $^{19}F$ MRI will thus be necessarily based on the use of added $^{19}F$ contrast agents.

Contrast agents for $^{19}F$ MRI preferably have a large number of magnetically equivalent fluoro-groups (the sensitivity scales linearly with the number of magnetically equivalent F atoms per molecule). With a view to the desired combination with CEST MRI, the $^{19}F$ MR contrast agents used are preferably water-soluble, and particularly are preferably charged molecules so as to have as high a watersolubility as possible. With a view to application in phospholipid shells, the preferred $^{19}$F contrast agents do not significantly bind, or are not significantly associated with phospholipids. With a view to their release in the human or animal body, the $^{19}$F contrast agents are preferably of low toxicity and high biocompatibility.

Figure 1:
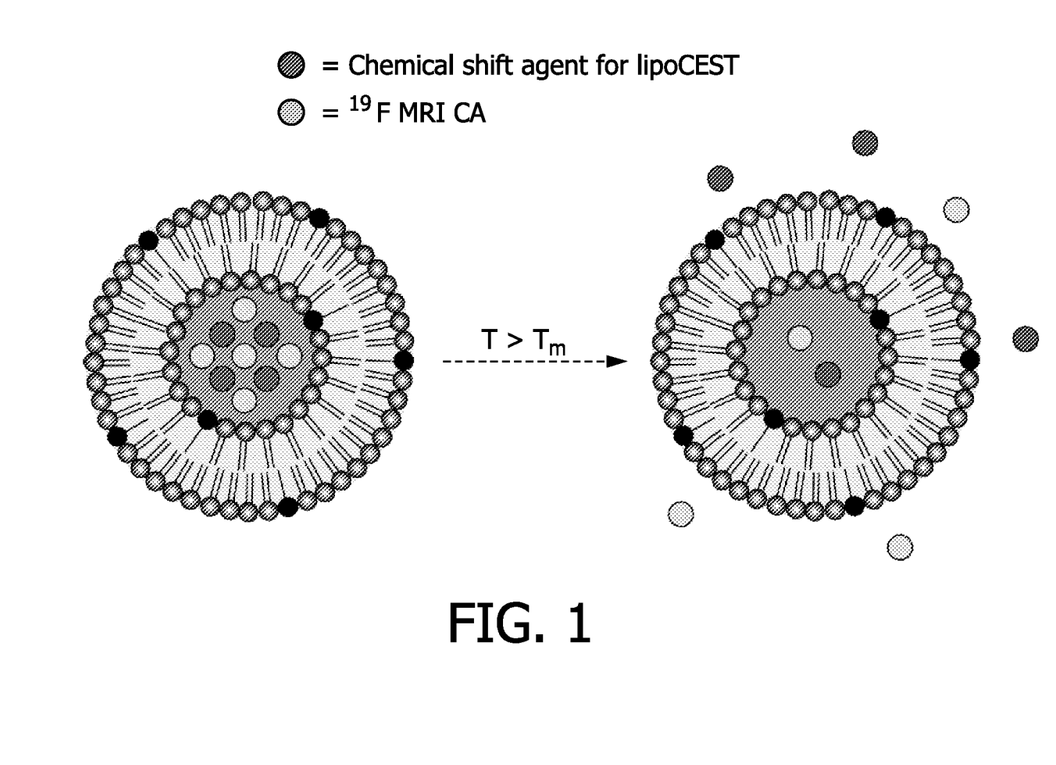
FIG. 1_A thermo-sensitive liposome for image-guided delivery of drug molecules. The schematic representation shows the release of a chemical shift agent (e.g. [Tm (hpdo3a)H$_2$O]) and a $^{19}F$ MRI contrast agents (e.g. NH$_4$PF$_6$) upon the application of an external trigger (e.g. heating, ultrasound or RF).
Figure 2:
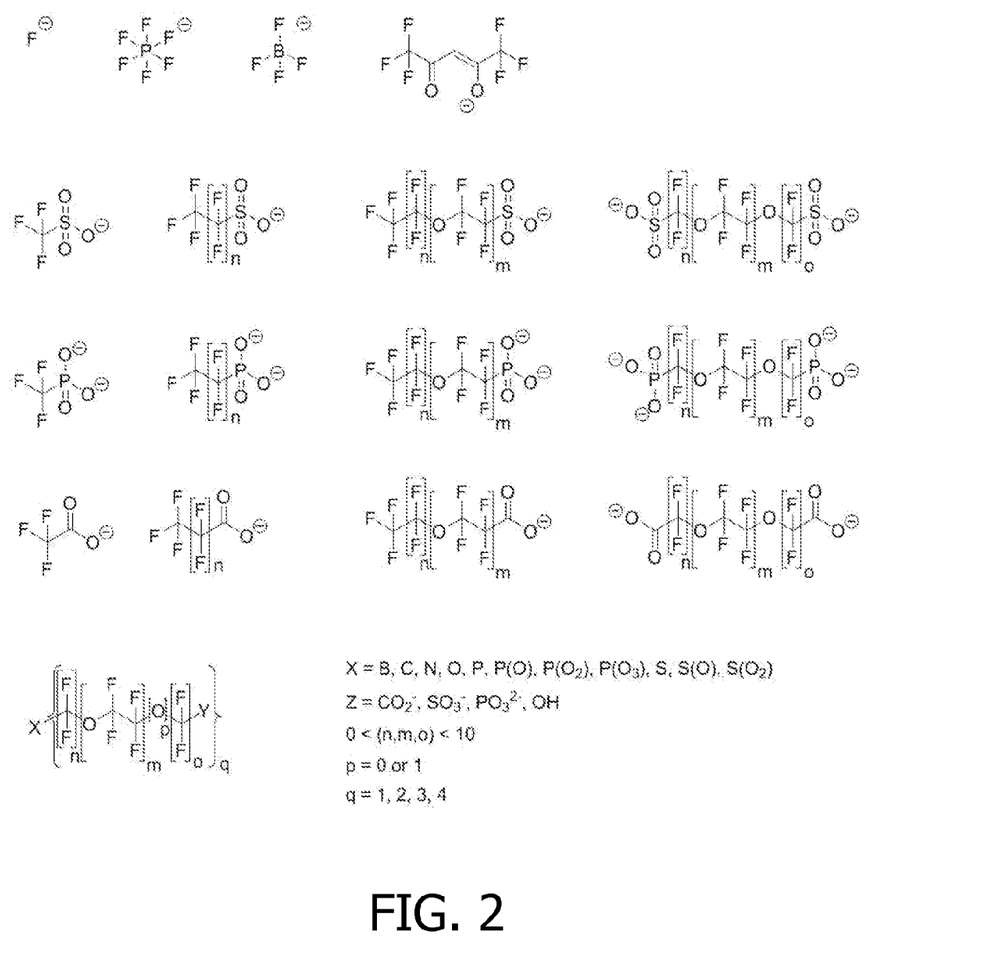
FIG. 2 Examples of suitable contrast agents for $^{19}F$ MRI.
Figure 3:
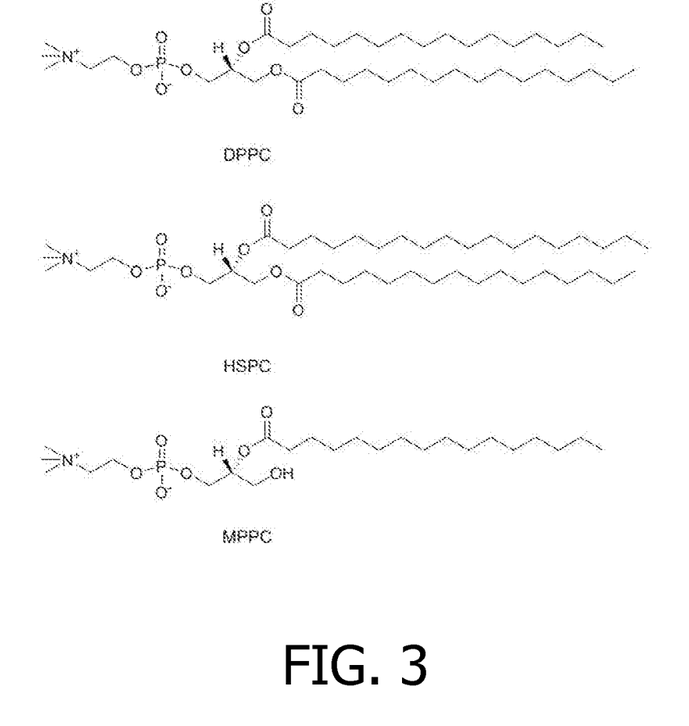
FIG. 3 Chemical formulas of dipalmitoyl sn-glycero-3-phosphocholine (DPPC), hydrogenated soy sn-glycero-3-phosphocholine (HSPC), and monopalmitoyl sn-glycero-3-phosphocholine (MPPC).
Figure 4:
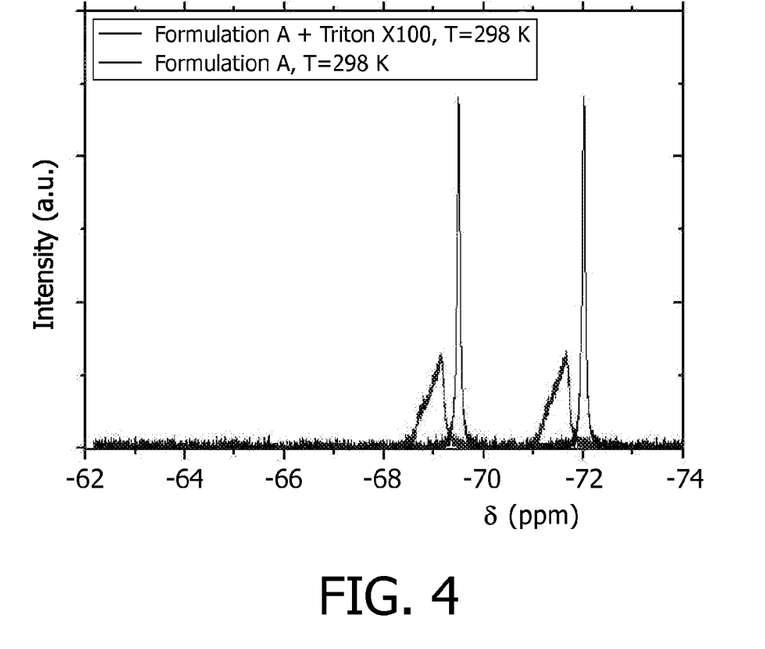
FIG. 4 $^{19}F$ NMR signal of liposomes with 50 mM of NH$_4$PF$_6$ in the lumen (formulation A) at 7 T. Upon addition of Triton-X100, a non ionic surfactant, the $^{19}F$ signal become sharper, indicative for the release of NH$_4$PF$_6$ from the inside of the liposome.
Figure 5:
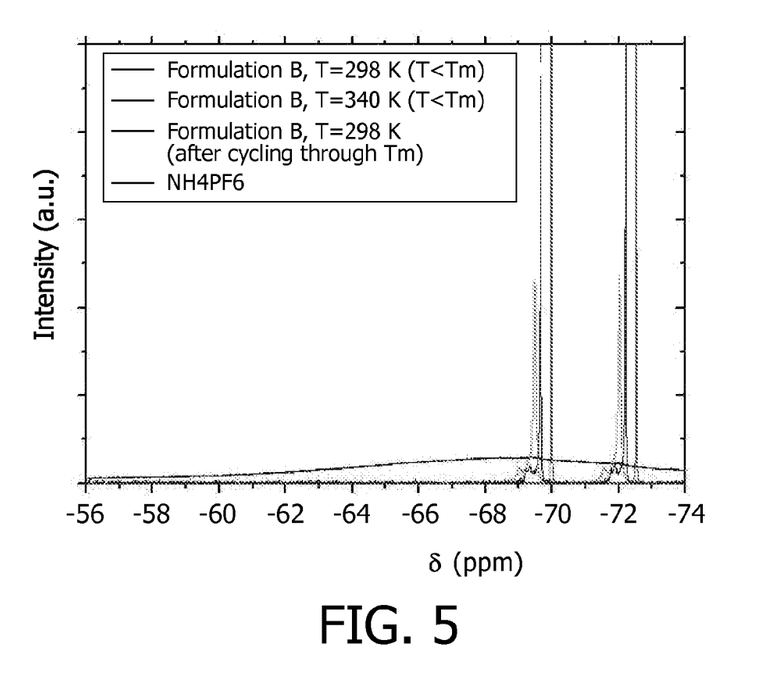
FIG. 5 $^{19}F$ NMR spectra of low-temperature-sensitive liposomes (formulation B), containing NH$_4$PF$_6$ and [Tm (hpdo3a)(H$_2$O)], at different temperatures.
Figure 6:
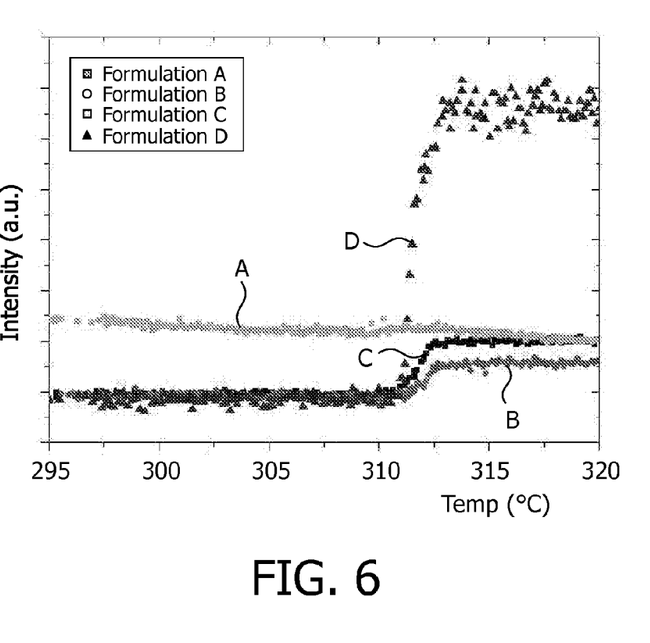
FIG. 6 The intensity of the $^{19}F$ NMR signal of low-temperature-sensitive liposomes (LTSL) with different concentrations of encapsulated NH$_4$PF$_6$ (formulation A-D) as a function of temperature at 7 T, showing the increase of the intensity of the $^{19}F$ signal at the melting phase transition temperature upon temperature increase.
Figure 7:
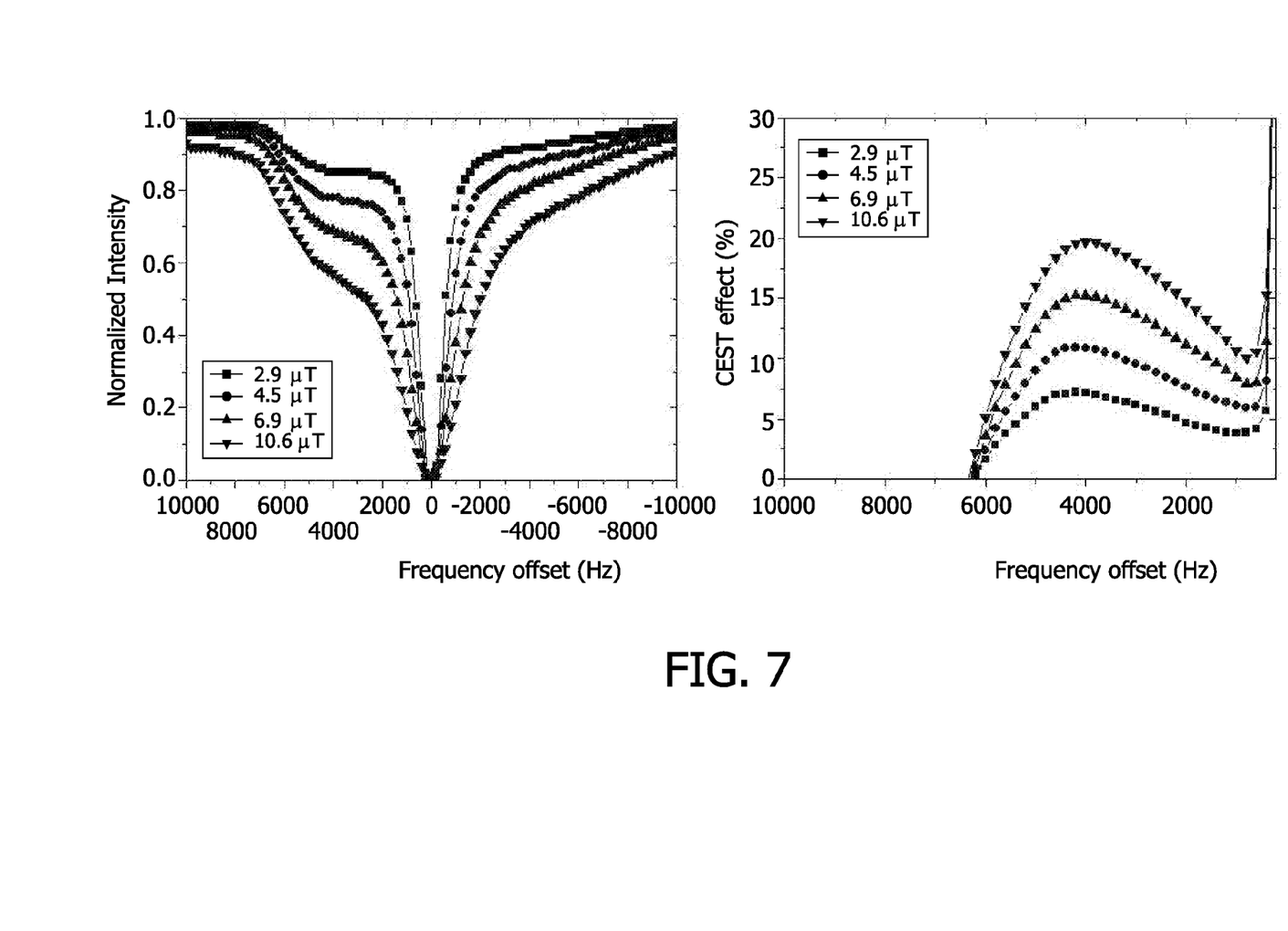
FIG. 7 Z spectra (left) and CEST effects (right) of low-temperature-sensitive liposomes loaded with 50 mM [Tm(hpdo3a)(H$_2$O)] and 50 mM NH$_4$PF$_6$ (formulation B) as a function of the presaturation power level (2.9-10.6 µT) at 298 K and 7.0 T. The CEST effect was calculated according to equation: $(1-M_s/M_0)*100\%$, where $M_s$ is the magnitude of the water proton signal after selective saturation of the intraliposomal water pool and $M_0$ is the intensity of the bulk water proton signal under control irradiation at the opposite frequency offset.
Figure 8:
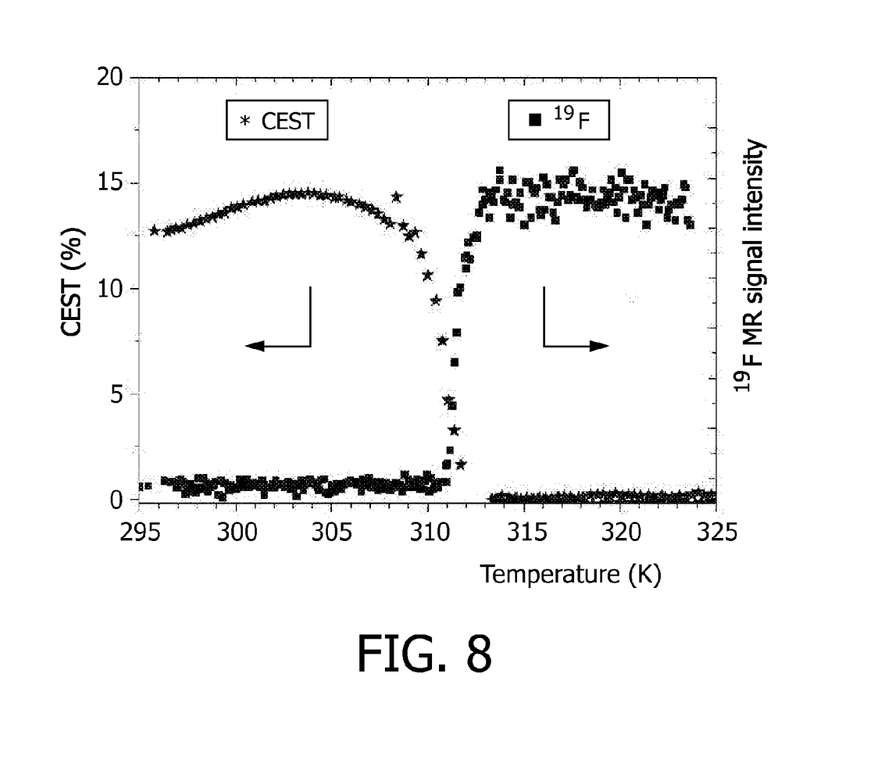
FIG. 8 NMR signal intensity of low-temperature-sensitive liposomal contrast agents for CEST $^1H$ and $^{19}F$ MRI as a function of temperature (formulation B).
Figure 9:
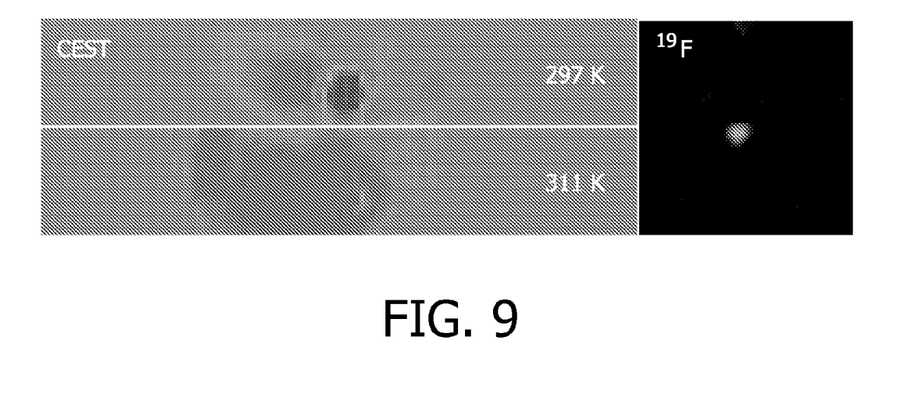
FIG. 9 CEST images of low-temperature-sensitive liposomal MRI contrast agents (formulation B) acquired using a simultaneous dual $^{19}F/^1H$ sequence at 3 T. The CEST effect observed at 297 K disappeared at 311 K, indicative of the release of [Tm(hpdo3a)(H$_2$O)] from the inside of the liposome (left). After heating of the agent, the $^{19}F$ MR signal becomes visible (right).
Figure 10:
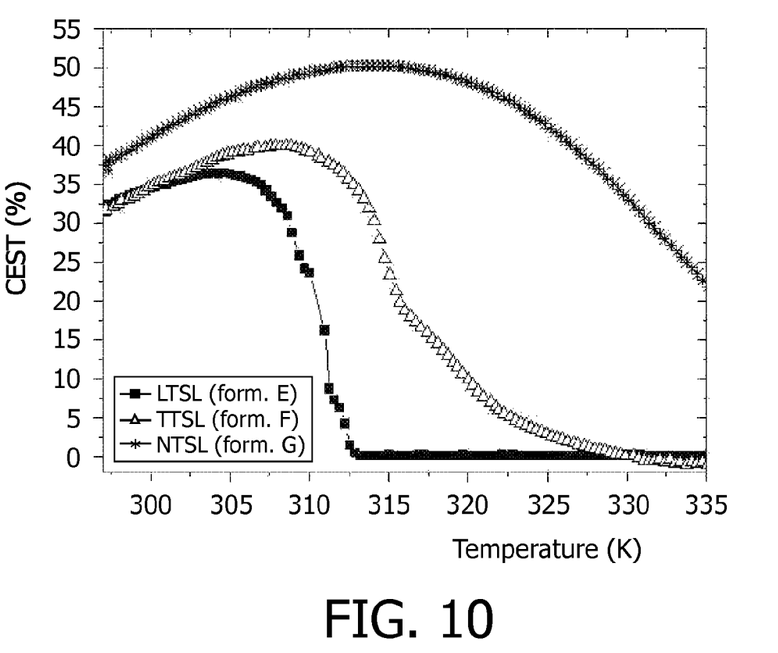
FIG. 10 CEST effect versus temperature for low temperature sensitive liposomes (LTSL) (formulation E), traditional temperature sensitive liposomes (TTSL) (formulation F), and non temperature sensitive liposomes (NTSL) (formulation G). Low-temperature-sensitive liposomal CEST MRI contrast agents (formulation E) display a sharp decrease of the CEST effect at 312 K, whereas a slower decrease of the CEST effect is observed at higher temperatures for CEST MRI contrast agents based on either TTSL or NTSL.
Figure 11:
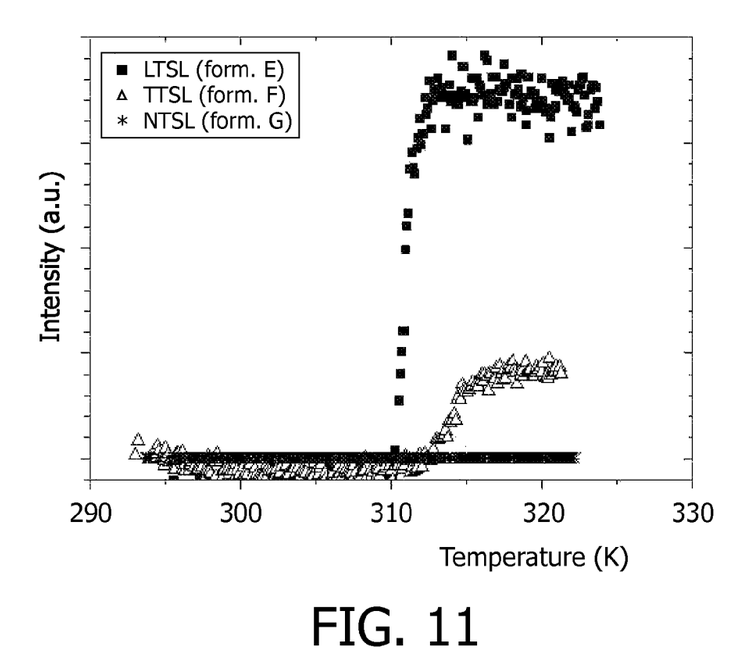
FIG. 11 $^{19}F$ signal versus temperature for LTSL (formulation E), TTSL (formulation F), and NTSL (formulation G).

Preferred $^{19}$F contrast agents are selected from the compounds depicted in FIG. 2, and mixtures thereof. Most preferably, charged per-F analogs of aliphatic hydrocarbons are employed.

CEST MRI

The invention, in a preferred embodiment, also relates to CEST MRI contrast enhancement. This method serves to generate image contrast by utilizing Chemical Exchange-dependent Saturation Transfer (CEST) from selected, magnetically pre-saturated protons to the bulk water molecules determined by MRI.

Although the invention, in this preferred embodiment, relates to the application of any CEST-type contrast enhancement to thermosensitive drug release, it is preferred to make use of more advanced CEST methods as have become available.

CEST in combination with a paramagnetic chemical shift reagent (ParaCEST) is a method, in which the magnetization of a pool of paramagnetically shifted protons of a CEST contrast agent is selectively saturated by the application of radio frequency (RF) radiation. The transfer of this saturation to bulk water molecules by proton exchange leads to a reduced amount of excitable water protons in the environment of the CEST contrast agent. Thus a decrease of the bulk water signal intensity is observed, which can be used to create a (negative) contrast enhancement in MRI images.

An approach to obtain a high CEST efficiency is based on utilizing the large number of water molecules of a solution containing a paramagnetic shift reagent (e.g. Na[Tm(dotma)(H$_2$O)]), wherein "H$_4$dotma" stands for α,α',α,"α'"-tetramethyl-1,4,7,10-tetraacetic acid and dotma represents the respective fourfold deprotonated tetraanionic form of the ligand, to provide a pool of protons that are chemically shifted and that, therefore, can selectively be saturated by an RF pulse. If this system is encapsulated in a carrier, e.g. a liposome, the magnetic saturation can be transferred to the bulk water molecules at the outside of the carriers, which are not chemically shifted (LipoCEST). The amount of magnetization transfer and hence the extent of contrast enhancement is determined by the rate of the diffusion of water through the shell of the carrier, e.g. a phospholipid membrane, as well as by the amount of water within the carrier.

The optimum water exchange rate is directly correlated with the chemical shift difference between the proton pool inside of the carrier and the bulk water outside of the carrier. The paramagnetic shift that is induced on the water molecules inside the liposomes consists of two main contributions: chemical shift resulting from a direct dipolar interaction between the water molecules and the shift reagent ($\delta_{dip}$), and chemical shift caused by a bulk magnetic susceptibility effect ($\delta_{bms}$). The overall paramagnetic shift is the sum of these two contributions:

$$\delta = \delta_{dip} + \delta_{bms} \quad (1)$$

$\delta_{bms}$ is zero for spherical particles, but it can be significant for anisotropic particles. The aspherical particles experience a force in a magnetic field, which causes them to align with the magnetic field lines. In the case of liposomes, this effect is further increased, if they bear paramagnetic molecules associated with the phospholipid membrane.

A reference on CEST using aspherical liposomes is Terreno, E. et al. Angew. Chem. Int. Ed. 46, 966-968 (2007).

Combined $^{19}$F and $^{1}$H MR Contrast Enhancement

With the invention a suitable combination of $^{19}$F and $^{1}$H MR can be realized in various ways.

Thus, a dual or multiple-label MR contrast can be generated by utilizing a CEST mechanism and/or $^{19}$F MR. Alternatively, multiple MR contrasts may be generated through the modification of the longitudinal relaxation time ($T_1$), or the transverse relaxation time ($T_2$) of the imaged analyte (typically the protons of water) by a metal-containing compound present in the carrier. Any of these contrast enhancing mechanisms may further be used in any combination thereof.

The dual/multiple labeled MRI contrast, depending on the physical state of the carrier, is monitored either in a subsequent or interleaved manner with conventional MR equipment—or simultaneously, using sequence combinations on dual-tuned spectrometer systems e.g. at $^{1}$H and $^{19}$F MR resonance frequencies.

In this respect the invention also relates to the use of simultaneous dual nuclei MR imaging in monitoring and/or guiding drug delivery.

The combination of a CEST and a $^{19}$F contrast agent in a thermo-sensitive liposome offers the opportunity to monitor the drug release process independently and simultaneously by means of CEST and $^{19}$F MRI. Simultaneous monitoring of the two different MR signals is mediated by corresponding dual-label MR techniques. This approach leads to several possible advantages. Thus, the spatial distribution of the drug-loaded particles can be assessed prior to drug release by means of CEST MRI; the $^{1}$H CEST and the $^{19}$F MR signals scale with the amount of released drug, which allows for quantitative control of the delivered drug dose in vivo using a feedback loop; the release of drugs from the carrier at the diseased site can be induced by a local stimulus, such as heating in the case of thermosensitive liposomes using e.g. RF or ultrasound; the CEST MR contrast enhancement can be switched on and off at will.

Carrier

In the foregoing, reference is made to a carrier suitable for the localized delivery of a biologically active agent, such as a drug. Hereinafter, the term "biologically active agent" will be referred to, in short, as "drug" and the carrier as a "drug carrier."

A drug carrier in the context of the present invention refers to any material in or on which a bio-active agent can be contained so as to be capable of being released in the body of a subject.

Suitable carriers include microcarriers and, particularly nanocarriers such as liposomes, polymersomes, nanocapsules and other dosage forms of a size or nature commensurate with a use as a CEST contrast agent.

The drug carrier is to be introduced into the body of a person to be subjected to MRI. This will be e.g. by injection in the blood stream, or by other methods to introduce the carrier into body fluid.

A drug is a chemical substance used in the treatment, cure, prevention, or diagnosis of a disease or disorder, or used to otherwise enhance physical or mental well-being. The guided delivery foreseen with the present invention will mostly be useful therapeutic agents (i.e. drugs in a strict sense, intended for therapy or prevention of diseases or disorders), but also for agents that are administered for diagnostic purposes. Although other bio-active agents, i.e. those that are not therapeutic or diagnostic, such as functional food ingredients, will not generally be subjected to guided and/or monitored delivery, such could be done using the present invention if desired.

The most optimal use of the invention is attained in the case of targeted therapeutics, i.e. drugs that are intended for targeted delivery, as such delivery will by nature benefit most from the monitoring made available by the invention. This pertains, e.g., to agents in the treatment of tumors to be delivered on site, to agents in the treatment or prevention of cardiovascular disorders, such as atherosclerosis in the coronary arteries, or to antithrombotic agents (e.g. for locally resolving blood cloths) or agents that require passing the blood-brain barrier such as neuromodulators as can be used in the treatment of neural conditions such as epilepsy, Alzheimer's disease, Parkinson's disease, or stroke. Benefits from the guidance and monitoring of targeted drug delivery are also applicable to targeted diagnostic agents. Similarly as with targeted therapeutics, here too cancer is an area where site-specific delivery can be of importance.

Bio-active agents suitable for use in the present invention include biologically active agents including therapeutic drugs, endogenous molecules, and pharmacologically active agents, including antibodies; nutritional molecules; cosmetic agents; diagnostic agents; and additional contrast agents for imaging. As used herein, an active agent includes pharmacologically acceptable salts of active agents.

The drug carriers of the present invention can comprise either hydrophilic or hydrophobic bioactive agents. A hydrophilic bioactive agent could be encapsulated in the aqueous compartment of the carrier, whereas hydrophobic bioactive agents could be incorporated in hydrophobic domains of the carrier, for instance in the lipid bilayer of liposomes. Nucleic acids, carbohydrates and, in general, proteins and peptides are water soluble or hydrophilic. For instance, bioactive agents which are small molecules, lipids, lipopolysaccharides, polynucleotides and antisense nucleotides (gene therapy agents) are also envisaged. Such biologically active agents, which may be incorporated, thus include non-peptide, non-protein drugs. It is possible within the scope of the present invention to incorporate drugs of a polymeric nature, but also to incorporate drugs of a relatively small molecular weight of less than 1500 g/mol, or even less than 500 g/mol.

Accordingly, compounds envisaged for use as bioactive agents in the context of the present invention include any compound with therapeutic or prophylactic effects. It can be a compound that affects or participates in tissue growth, cell growth, cell differentiation, a compound that is able to invoke a biological action such as an immune response, or a compound that can play any other role in one or more biological processes. A non-limiting list of examples includes antimicrobial agents (including antibacterial, anti-viral agents and anti-fungal agents), anti-viral agents, anti-tumor agents, thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, anti metabolites, antiproliferatives (including antiangiogenesis agents), anticancer chemotherapeutic agents, anti-inflammatory steroid or non-steroidal anti-inflammatory agents, immunosuppressive agents, growth hormone antagonists, growth factors, dopamine agonists, radiotherapeutic agents, extracellular matrix components, ACE inhibitors, free radical scavengers, chelators, antioxidants, anti polymerases, and photodynamic therapy agents.

Relatively small peptides may be referred to by the number of amino acids (e.g. di-, tri-, tetrapeptides). A peptide with a relatively small number of amide bonds may also be called an oligopeptide (up to 50 amino acids), whereas a peptide with a relatively high number (more than 50 amino acids) may be called a polypeptide or protein. In addition to being a polymer of amino acid residues, certain proteins may further be characterized by the so called quaternary structure, a conglomerate of a number of polypeptides that are not necessarily chemically linked by amide bonds but are bonded by forces generally known to the skilled professional, such as electrostatic forces and Vanderwaals forces. The term peptides, proteins or mixtures thereof as used herein is to include all above mentioned possibilities.

Usually, the protein and/or peptide are selected on the basis of its biological activity. Depending on the type of polymer chosen, the product obtainable by the present process is highly suitable for controlled release of proteins and peptides. In a particular embodiment, the protein or peptide is a growth factor.

Other examples of peptides or proteins or entities comprising peptides or proteins, which may advantageously be contained in the loaded polymer include, but are not limited to, immunogenic peptides or immunogenic proteins, which include, but are not limited to, the following:

Toxins such as diphtheria toxin and tetanus toxin.

Viral surface antigens or parts of viruses such as adenoviruses, Epstein-Barr Virus, Hepatitis A Virus, Hepatitis B Virus, Herpes viruses, HIV-1, HIV-2, HTLV-III, Influenza viruses, Japanese encephalitis virus, Measles virus, Papilloma viruses, Paramyxoviruses, Polio Virus, Rabies, Virus, Rubella Virus, Vaccinia (Smallpox) viruses and Yellow Fever Virus.

Bacterial surface antigens or parts of bacteria such as *Bordetella pertussis, Helicobacter pylori, Clostridium tetani, Corynebacterium diphtheria, Escherichia coli, Haemophilus influenza, Klebsiella* species, *Legionella pneumophila, Mycobacterium bovis, Mycobacterium leprae, Mycrobacterium tuberculosis, Neisseria gonorrhoeae, Neisseria meningitidis, Proteus* species, *Pseudomonas aeruginosa, Salmonella* species, *Shigella* species, *Staphylococcus aureus, Streptococcus pyogenes, Vibrio cholera* and *Yersinia pestis*.

Surface antigens of parasites causing disease or portions of parasites such as *Plasmodium vivax* (malaria), *Plasmodium falciparum* (malaria), *Plasmodium ovale* (malaria), *Plasmodium malariae* (malaria), *Leishmania tropica* (leishmaniasis), *Leishmania donovani*), leishmaniasis), *Leishmania branziliensis* (leishmaniasis), *Trypanosoma rhodescense* (sleeping sickness), *Trypanosoma gambiense* (sleeping sickness), *Trypanosoma cruzi* (Chagas' disease), *Schistosoma mansoni* (schistosomiasis), *Schistosomoma haematobium* (schistomiasis), *Schistosoma japonicum* (shichtomiasis), *Trichinella spiralis* (trichinosis), *Stronglyloides duodenale* (hookworm), *Ancyclostoma duodenale* (hookworm), *Necator americanus* (hookworm), *Wucheria bancrofti* (filariasis), *Brugia malaya* (filariasis), *Loa boa* (filariasis), *Dipetalonema perstaris* (filariasis), *Dracuncula medinensis* (filariasis), and *Onchocerca volvulus* (filariasis).

Immunoglobulins such as IgG, IgA, IgM, Antirabies immunoglobulin, and Antivaccinia immunoglobulin.

Antitoxin such as *Botulinum* antitoxin, diphtheria antitoxin, gas gangrene antitoxin, tetanus antitoxin.

Antigens which elicit an immune response against foot and mouth disease.

Hormones and growth factors such as follicle stimulating hormone, prolactin, angiogenin, epidermal growth factor, calcitonin, erythropoietin, thyrotropic releasing hormone, insulin, growth hormones, insulin-like growth factors 1 and 2, skeletal growth factor, human chorionic gonadotropin, luteinizing hormone, nerve growth factor, adrenocorticotropic hormone (ACTH), luteinizing hormone releasing hormone (LHRH), parathyroid hormone (PTH), thyrotropin releasing hormone (TRH), vasopressin, cholecystokinin, and corticotropin releasing hormone; cytokines, such as interferons, interleukins, colony stimulating factors, and tumor necrosis factors: fibrinolytic enzymes, such as urokinase, kidney plasminogen activator; and clotting factors, such as Protein C, Factor VIII, Factor IX, Factor VII and Antithrombin III.

Examples of other proteins or peptides are albumin, atrial natriuretic factor, renin, superoxide dismutase, alpha 1-antitrypsin, lung surfactant proteins, bacitracin, bestatin, cydosporine, delta sleep-inducing peptide (DSIP), endorphins, glucagon, gramicidin, melanocyte inhibiting factors, neurotensin, oxytocin, somostatin, terprotide, serum thymide factor, thymosin, DDAVP, dermorphin, Met-enkephalin, peptidoglycan, satietin, thymopentin, fibrin degradation product, des-enkephalin-alpha-endorphin, gonadotropin releasing hormone, leuprolide, alpha-MSH and metkephamid.

Anti-tumor agents such as altretamin, fluorouracil, amsacrin, hydroxycarbamide, asparaginase, ifosfamid, bleomycin, lomustin, busulfan, melphalan, chlorambucil, mercaptopurin, chlormethin, methotrexate, cisplatin, mitomycin, cyclophosphamide, procarbazin, cytarabin, teniposid, dacarbazin, thiotepa, dactinomycin, tioguanin, daunorubicin, treosulphan, doxorubicin, tiophosphamide, estramucin, vinblastine, etoglucide, vincristine, etoposid, vindesin and paclitaxel.

Antimicrobial agents comprising:

Antibiotics such as ampicillin, nafcillin, amoxicillin, oxacillin, azlocillin, penicillin G, carbenicillin, penicillin V, dicloxacillin, phenethicillin, floxacillin, piperacillin, mecillinam, sulbenicillin, methicillin, ticarcillin, mezlocillin, Cephalosporins: cefaclor, cephalothin, cefadroxil, cephapirin, cefamandole, cephradine, cefatrizine, cefsulodine, cefazolin, ceftazidim, ceforanide, ceftriaxon, cefoxitin, cefuroxime, cephacetrile, latamoxef, and cephalexin. Aminoglycosides such as amikacin, neomycin, dibekacyn, kanamycin, gentamycin, netilmycin, tobramycin. Macrolides such as amphotericin B, novobiocin, bacitracin, nystatin, clindamycin, polymyxins, colistin, rovamycin, erythromycin, spectinomycin, lincomycin, vancomycin Tetracyclines such as chlortetracycline, oxytetracycline, demeclocycline, rolitetracycline, doxycycline, tetracycline and minocycline. Other antibiotics such as chloramphenicol, rifamycin, rifampicin and thiamphenicol.

Chemotherapeutic agents such as the sulfonamides sulfadiazine, sulfamethizol, sulfadimethoxin, sulfamethoxazole, sulfadimidin, sulfamethoxypyridazine, sulfafurazole, sulfaphenazol, sulfalene, sulfisomidin, sulfamerazine, sulfisoxazole and trimethoprim with sulfamethoxazole or sulfametrole.

Urinary tract antiseptics such as methanamine, quinolones (norfloxacin, cinoxacin), nalidixic acid, nitro-compounds (nitrofurantoine, nifurtoinol) and oxolinic acid.

Drug for anaerobic infections such as metronidazole.

Drugs for tuberculosis such as aminosalicyclic acid, isoniazide, cycloserine, rifampicine, ethambutol, tiocarlide, ethionamide and viomycin.

Drugs for leprosy such as amithiozone, rifampicine, clofazimine, sodium sulfoxone and diaminodiphenylsulfone (DDS, dapsone).

Antifungal agents such as amphotericin B, ketoconazole, clotrimazole, miconazole, econazole, natamycin, flucytosine, nystatine and griseofulvin.

Antiviral agents such as aciclovir, idoxuridine, amantidine, methisazone, cytarabine, vidarabine and ganciclovir.

Chemotherapy of amebiasis such as chloroquine, iodoquinol, clioquinol, metronidazole, dehydroemetine, paromomycin, diloxanide, furoatetinidazole and emetine.

Anti-malarial agents such as chloroquine, pyrimethamine, hydroxychloroquine, quinine, mefloquine, sulfadoxine/pyrimethamine, pentamidine, sodium suramin, primaquine, trimethoprim and proguanil.

Anti-helminthiasis agents such as antimony potassium tartrate, niridazole, antimony sodium dimercaptosuccinate, oxamniquine, bephenium, piperazine, dichlorophen, praziquantel, diethylcarbamazine, pyrantel parmoate, hycanthone, pyrivium pamoate, levamisole, stibophen, mebendazole, tetramisole, metrifonate, thiobendazole and niclosamide.

Anti-inflammatory agents such as acetylsalicyclic acid, mefenamic acid, ado fenac, naproxen, azopropanone, niflumic acid, benzydamine, oxyphenbutazone, diclofenac, piroxicam, fenoprofen, pirprofen, flurbiprofen, sodium salicyclate, ibuprofensulindac, indomethacin, tiaprofenic acid, ketoprofen and tolmetin.

Anti-gout agents such as colchicine and allopurinol.

Centrally acting (opoid) analgesics such as alfentanil, methadone, bezitramide, morphine, buprenorfine, nicomorphine, butorfanol, pentazocine, codeine, pethidine, dextromoramide, piritranide, dextropropoxyphene, sufentanil and fentanyl.

Local anesthetics such as articaine, mepivacaine, bupivacaine, prilocaine, etidocaine, procaine, lidocaine and tetracaine.

Drugs for Parkinson's disease such as amantidine, diphenhydramine, apomorphine, ethopropazine, benztropine mesylate, lergotril, biperiden, levodopa, bromocriptine, lisuride, carbidopa, metixen, chlorphenoxamine, orphenadrine, cycrimine, procyclidine, dexetimide and trihexyphenidyl.

Centrally active muscle relaxants such as baclofen, carisoprodol, chlormezanone, chlorzoxazone, cyclobenzaprine, dantrolene, diazepam, febarbamate, mefenoxalone, mephenesin, metoxalone, methocarbamol and tolperisone.

Corticosteroids comprising:

Mineralocorticosteroids such as cortisol, desoxycorticosterone and flurohydrocortisone.

Glucocorticosteroids such as beclomethasone, betamethasone, cortisone, dexamethasone, fluocinolone, fluocinonide, fluocortolone, fluorometholone, fluprednisolone, flurandrenolide, halcinonide, hydrocortisone, medrysone, methylprednisolone, paramethasone, prednisolone, prednisone and triamcinolone (acetonide).

Androgens comprising:

Androgenic steroids used in therapy such as danazole, fluoxymesterone, mesterolone, methyltestosterone, testosterone and salts thereof.

Anabolic steroids used in therapy such as calusterone, nandrolone and salts thereof, dromostanolone, oxandrolone, ethylestrenol, oxymetholone, methandriol, stanozolol methandrostenolone and testolactone.

Antiandrogens such as cyproterone acetate.

Estrogens comprising estrogenic steroids used in therapy such as diethylstilbestrol, estradiol, estriol, ethinylestradiol, mestranol and quinestrol.

Anti-estrogens such as chlorotrianisene, clomiphene, ethamoxytriphetol, nafoxidine and tamoxifen.

Progestins such as allylestrenol, desogestrel, dimethisterone, dydrogesterone, ethinylestrenol, ethisterone, ethynadiol diacetate, etynodiol, hydroxyprogesterone, levonorgestrel, lynestrenol, medroxyprogesterone, megestrol acetate, norethindrone, norethisterone, norethynodrel, norgestrel, and progesterone.

Thyroid drugs comprising:

Thyroid drugs used in therapy such as levothyronine and liothyronine

Anti-thyroid drugs used in therapy such as carbimazole, methimazole, methylthiouracil and propylthiouracil.

Apart from bioactive agents which are water soluble, other water-soluble compounds can be incorporated such as anti-oxidants, ions, chelating agents, dyes, imaging compounds.

Preferred therapeutic agents are in the area of cancer (e.g. antitumor) and cardiovascular disease.

Methods of preparing lipophilic drug derivatives which are suitable for nanoparticle or liposome formulation are known in the art (see e.g., U.S. Pat. No. 5,534,499 describing covalent attachment of therapeutic agents to a fatty acid chain of a phospholipid). Drugs in the present invention can also be prodrugs.

The drug may be present in the inner, the outer, or both of the compartments of the carrier, e.g. in the cavity and/or in the shell of a liposome. The distribution of the drug is independent of the distribution of any other agents comprised in the drug carrier, such as a paramagnetic chemical shift reagent or a paramagnetic agent. A combination of drugs may be used and any of these drugs may be present in the inner, the outer, or both of the compartments of the drug carrier, e.g. in the cavity and/or in the shell of a liposome.

Thermosensitive Carriers

The invention preferably provides for carriers that are thermosensitive. This means that the physical or chemical state of the carrier is dependent on its temperature.

Any thermosensitive carrier that can package a molecule of interest and that is intact at body temperature (i.e. 37° C.) but destroyed at any other, non-body temperature that can be tolerated by a subject may be used. Carriers of the invention include but are not limited to thermosensitive micro- and nanoparticles, thermosensitive polymersomes, thermosensitive liposomes, thermosensitive nanovesicles and thermosensitive nanospheres.

Thermosensitive nanovesicles generally have a diameter of up to 100 nm. In the context of this invention, vesicles larger than 100 nm, typically up to 5000 nm, are considered as microvesicles. The word vesicle describes any type of micro- or nanovesicle. Vesicles, such as liposomal vesicles, typically include a cavity which may contain any substance of interest. In the invention this is preferred, as outlined above.

Thermosensitive nanospheres include but are not limited to spheres which are no smaller than 5 nanometers. Nanospheres typically do not contain a cavity, i.e. in this embodiment of the invention the CEST effect should be realized purely by chemically shifted protons of the paramagnetic chemical shift agent itself that is comprised in the nanosphere.

Thermosensitive polymersomes include but are not limited to any polymer vesicle, including microvesicles and nanovesicles.

Thermosensitive liposomes include but are not limited to any liposome, including those having a prolonged half-life, e.g. PEGylated liposomes.

In order to make use of an optimal CEST contrast enhancement, it is preferred to employ thermosensitive carriers that have a semipermeable shell enclosing a cavity, such as liposomes. The advantage hereof is that the CEST contrast enhancement can be conducted on the basis of a paramagnetic chemical shift agent contained in the cavity, in interaction with a pool of protons or other MRI analytes also present in the cavity.

The term "semipermeable" is well understood in the art. In general it refers to the property of a membrane, such as a shell, to be selectively permeable, sometimes also denoted partially or differentially permeable. A shell in this sense indicates a structure that basically is closed in the sense that it is a not fully open wall, and preferably a mostly closed wall, (in this case a shell enclosing a cavity), that allows certain molecules or ions to pass through it by diffusion.

In this description, the semipermeability of the shell generally refers to its ability to allow the MR analyte to pass through it by diffusion. Hence, if the combination of analyte (such as water, or other small molecules comprising protons) and shell (such as a lipid bilayer) is such that the analyte is capable of passing through the shell by diffusion, the shell is considered semipermeable.

References on thermosensitive carriers having a semipermeable shell, are e.g. U.S. Pat. No. 6,726,925, US 2006/0057192, US 2007/0077230A1 and JP 2006-306794. Based on the description of this invention, the reference to these disclosures will enable the person skilled in the art to execute CEST contrast enhancement using thermosensitive liposomes.

Liposomes are generally spherical vesicles comprising a bilayer membrane enclosing a cavity, or lumen. The bilayer can be made up of at least one phospholipid and may or may not comprise cholesterol. Liposomes can be composed of naturally-derived phospholipids with mixed lipid chains (like egg phosphatidylethanolamine), or of pure surfactant components like dioleoylphosphatidylethanolamine (DOPE). The term liposomes, as used in the description of the invention, includes lipid spheres usually denoted micelles.

A typical example of a semipermeable shell is also found in semipermeable membranes comprising a phospholipid bilayer. A phospholipid bilayer is the most permeable to small, uncharged solutes. Liposomes can be made on the basis of a phospholipid bilayer.

Thermosensitive liposomes for use in the invention ideally retain their structure at about 37°, i.e. human body temperature, but are destroyed at a higher temperature, preferably only slightly elevated above human body temperature, and preferably also above pyrexic body temperature. Typically about 42° C. is a highly useful temperature for thermally guided drug delivery.

The required heat to raise the temperature of the thermosensitive drug carriers so as to promote the destruction of the thermosensitive carriers may be used. Heat can be applied in any physiologically acceptable way, preferably by using a focused energy source capable of inducing highly localized hyperthermia. The energy can be provided through, e.g., microwaves, ultrasound, magnetic induction, infrared or light energy.

Thermosensitive liposomes are known in the art. Liposomes according to the present invention may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic, D. D., Liposomes from physics to applications, Elsevier Science Publishers, Amsterdam, 1993; Liposomes, Marcel Dekker, Inc., New York (1983).

Entrapment of a drug or other bio-active agent within liposomes of the present invention may also be carried out using any conventional method in the art. In preparing liposome compositions of the present invention, stabilizers such as antioxidants and other additives may be used as long as they do not interfere substantially with the purpose of the invention.

Liposomes and other potential carriers based on a semipermeable shell enclosing a cavity will generally be spherical. For use in the invention, it is preferred to render such spherical carriers aspherical. E.g. in the case of liposomes, this is done by subjecting the liposomes to a dialysis process against a hypertonic buffer solution, hence a buffer solution with a higher osmolarity compared to the solution at the inside of the liposomes. The dialysis causes a net diffusion of water from the inside of the liposomes to the bulk solution. This reduces the total inner volume of the liposomes. Since the surface area of the liposomes remains constant, the volume reduction forces the liposomes to deform and to assume an aspherical shape, such as a disk shape, a cigar shape, or any other aspherical shape.

The Paramagnetic Chemical Shift Reagent

In the invention, a paramagnetic shift reagent can be comprised in any manner in or on the carrier. It is preferred to have the shift reagent in sufficient interaction with a pool of protons by comprising both the reagent and the pool in the cavity of the carrier.

The paramagnetic chemical shift reagent or reagents can basically be any paramagnetic agent suitable to render the relatively large number of water molecules of a solution or dispersion, in which it is contained, into a pool of protons that are chemically shifted regarding their MR resonance frequency, with respect to the surrounding protons of the bulk water molecules. As explained hereinbefore with respect to lipoCEST, the preferred thermosensitive drug carriers, in which the paramagnetic chemical shift reagent and the internal pool of protons are contained, can be saturated through an RF pulse. As the preferred drug carriers comprise a shell, such as the lipid bilayer membrane of liposomes that fundamentally allows exchange of protons with their direct environment, the saturation caused by the RF pulse will be transferred to the environment of the loaded, RF-saturated, thermosensitive drug carriers. Thus, upon conducting magnetic resonance imaging, the direct environment of the thermosensitive drug carriers will show a decreased signal intensity as compared to other bulk water molecules, and thus allows to detect the direct environment of the contrast agents due to a decreased signal intensity. The paramagnetic chemical shift reagent is to comprise a paramagnetic compound, i.e. any compound having paramagnetic properties. Preferably the paramagnetic compound comprises a paramagnetic metal, where the term metal refers to metallic nano- or microparticles, or metal ions, explicitly including metal ions complexed by chelate ligands. Paramagnetic metals are known to the skilled person, and do not require elucidation here. E.g., early and late transition metals, explicitly including chromium, manganese, iron, as well as lanthanides, such as gadolinium, europium, dysprosium, holmium, erbium, thulium, and ytterbium.

The paramagnetic chemical shift reagent is to comprise a chelating structure capable of strongly binding to the paramagnetic metal and allowing the metal to interact with water, or with another suitable source of protons. With respect to suitable chelating structures, reference is made to P. Caravan et al., Chem. Rev., 99, 2293-2352 (1999). Preferably the water is at least transiently coordinated to the metal of the paramagnetic reagent. With respect to chemical shift mechanisms, reference is made to J. A. Peeters et al., Prog. Nucl. Magn. Reson. Spectr, 28, 283-350 (1999). In one embodiment, the chelating structure itself also comprises exchangeable protons, e.g. hydroxy, amine, or amide protons.

Suitably, the paramagnetic chemical shift reagent comprises a lanthanide ion coordinated with a chelating structure, e.g. macrocylic lanthanide(III) chelates derived from 1,4,7,10-tetraazacyclododecane-1,4,7,10-tetraacetic acid ($H_4$dota), 1,4,7,10-tetraazacyclododecane-$\alpha,\alpha',\alpha'',\alpha'''$-tetramethyl-1,4,7,10-tetraacetic acid ($H_4$dotma), and related ligands that allow for an axially coordinated water molecule in the paramagnetic reagent. In this respect reference is made to Aime et al., Angew. Chem. Int. Ed., 44, 5513-5515 (2005).

Preferably, the paramagnetic chemical shift reagent is water-soluble. Suitable chemical shift reagents are known to the person skilled in the art. The CEST contrast agents do not require any specific chemical shift reagent, as long as the shift reagent and the pool of protons have a sufficient interaction to result in a pool of chemically shifted protons.

Preferably, the paramagnetic shift reagent is a metal complex comprising a metal ion and a ligand that is based on a multidentate chelate ligand. More preferably, the interaction of the chemical shift reagent with the pool of protons is provided in the form of coordination. Thus it is preferred for the metal complex to have at least one coordination site of the metal left open for the coordination of at least one water molecule.

Examples of suitable water-soluble chemical shift reagents are [Ln(hpdo3a)($H_2O$)] (1), [Ln(dota)($H_2O$)]$^-$ (2), [Ln(dotma)($H_2O$)]$^-$ (3), [Ln(dotam)($H_2O$)]$^{3+}$ (4), and [Ln(dtpa)($H_2O$)]$^{2-}$ (5), including derivatives thereof and related compounds, with Ln being a lanthanide ion.

Preferably the paramagnetic chemical shift reagent is a lanthanide complex such as in formulae 1-5 below:

[Ln(dotam)(H₂O)]³⁺

[Ln(dtpa)(H₂O)]²⁻ wherein the lanthanide is $Eu^{3+}$, $Dy^{3+}$, $Ho^{3+}$, $Er^{3+}$, $Tm^{3+}$, $Yb^{3-}$, and preferably is $Tm^{3+}$ or $Dy^{3+}$.

The paramagnetic chemical shift reagent is typically comprised in the agent in an amount of from 1 mM to 2000 mM, preferably of from 1 mM to 1000 mM, and more preferably of from 50 mM to 200 mM. The paramagnetic chemical shift agent may be an oligomeric or polymeric, oligo- or polynuclear compound comprising numerous paramagnetic metal ions per molecule.

Further Contrast Enhancement Agents

The thermosensitive drug carriers of the invention may comprise a $T_1$ or $T_2$ reduction agent. In this respect reference is made to Aime et al., JACS, 129, 2430-2431 (2007). In this way an all-in-one concept can be realized of $^{19}F$ MRI in combination with $T_1$, $T_2$, and preferably also with CEST contrast, in $^1H$ MRI.

The chemical shift difference to the saturation transfer protons in the environment of the thermosensitive drug carriers can be further enhanced by providing the thermosensitive drug carrier's membrane with a further paramagnetic agent, which is not necessarily a chemical shift reagent. Thus, the orientation of the aspherical carrier in the magnetic field is affected and the aforementioned bulk susceptibility effect is enhanced. The further paramagnetic agent is preferably an amphiphilic compound comprising a lanthanide complex (on the more polar side of the amphilic compound), and having an apolar tail, which has a tendency to preferably integrate in and align with the lipid bilayer at the thermosensitive drug carrier's surface based on hydrophobic molecular interactions.

These amphilic paramagnetic complexes can e.g. be:

6

7

8

9

10

The paramagnetic chemical shift reagent loaded thermosensitive drug carriers can advantageously be combined with paramagnetic agents in or at its outer surface, e.g. the liposome shell. Such agents generally comprise an amphiphilic compound bearing a paramagnetic group, preferably a lanthanide complex (on the more polar side of the amphilic compound), and having an apolar tail which has a tendency to preferably integrate in and align with the lipid bilayer at the preferred thermosensitive liposomes' surface based on hydrophobic molecular interactions.

The lanthanide ion in the optional membrane-associated paramagnetic agent may be identical with or different from the lanthanide within the cavity of the contrast agent.

As is provided according to the invention, the paramagnetic chemical shift reagent can be encapsulated in thermosensitive drug carriers. In this way a pool of water protons is created that has a different chemical shift compared to that of the bulk water surrounding the carriers. The magnetic resonance of these chemically-shifted water protons can be saturated with an RF pulse of a sufficiently narrow band width. Since the water molecules at the inside of the contrast agent are exchanging quickly with the bulk water molecules surrounding the contrast agents, this saturation is transferred to the bulk water.

Hence, when used in practice, at the location of a CEST contrast agent based on thermosensitive drug carriers, the surrounding water (i.e. body fluid in the preferred use in vivo) will be visible as hypointense areas in the CEST-enhanced MR images. With CEST-enhanced MRI, we mean conventional MRI wherein, prior to excitation, the exchangeable-water resonance has been selectively saturated. The RF pulse used for saturation typically has a band-width of several Hertz to several hundred Hertz. The appropriate frequency for the pulse is usually known a priori from phantom or preclinical CEST MRI studies, but can also be optimized during the actual clinical MRI examination.

Thus, the preferred carriers of the present invention (which do not only contain a $^{19}$F contrast agent, but also provide CEST contrast enhancement through the presence of a paramagnetic chemical shift agent and a pool of protons) are detectable not only by $^{19}$F MRI upon release of the $^{19}$F contrast agent, but also through $^1$H MRI at any point in time before the carrier is opened-up. If they additionally comprise $T_1$ or $T_2$ contrast agents, also the drug release step upon opening-up of the carrier can be detected (the CEST contrast enhancement will work as long as the shell is closed and exchange of saturated protons can occur through diffusion, the $T_1$ or $T_2$ contrast enhancement will display its action when these contrast agents are enabled to interact with bulk water (i.e. body fluid, when said agents are released through the opening up of the shell).

The carriers according to the invention can be used in a variety of ways. They can be applied to generate a desired level of MRI contrast in any aqueous environment. Its main use, which is also where the benefits of using thermosensitive drug carriers are enjoyed most, is to generate a local MRI contrast upon in vivo application. This can be by introducing the contrast agents, e.g. by injection into the blood or another body fluid of a living being, preferably a human being, and to perform a CEST contrast-enhanced MRI scan of the body, in whole or in part, of said being. The CEST contrast enhancement of bulk water molecules generated, allows the visibility of spots, such as tumors, where the regular body fluid presence is disturbed. Also, the contrast agents of the invention, in their lipid shell can be provided with disease-specific molecular probes, e.g. by having compounds possessing hydrophobic tail suitable to penetrate into the surface of the carrier (e.g. in the case of a phospholipid surface), wherein the other end of the compounds contains a ligand as desired. The thermosensitive drug carriers are designed to release their therapeutic content as activated at the biological target site, which corresponds to disintegration of the carrier shell. For most therapeutic nanocarriers, which are e.g. labeled by a LIPOCEST type MR contrast, the CEST MRI signal vanishes with the release process. Thus, the fate of the contained therapeutic material is no longer observable or quantifiable by MR. This is where the value of the $^{19}F$ signal for the medical application is particularly prominent. Arising with the drug release, the $^{19}F$ signal can be used to quantify the drug release process and to evaluate therapeutic efficacy. Depending on the molecular structure, the $^{19}F$ label can follow drug extravasation or tissue uptake, while the CEST nanocarrier label is confined to the conducting vessels.

This allows the contrast agents to preferentially locate at desired or suspect body sites which then can be made visible by MRI. This adds to the suitability of the drug carriers of the invention for localized delivery.

The CEST contrast agents of the invention preferably act on the basis of a pool of protons within the carrier, which exchange with fluid outside of the carrier. This exchange can be done by water-proton transfer, but also by proton transfer from other molecules small enough to pass the shell of the carrier, i.e. as preferred the lipid bilayer of thermosensitive liposomes.

It is to be understood that the invention is not limited to the embodiments and formulae as described hereinbefore. It is also to be understood that in the claims the word "comprising" does not exclude other elements or steps. Where an indefinite or definite article is used when referring to a singular noun e.g. "a" or "an", "the", this includes a plural of that noun unless something else is specifically stated.

EXAMPLE 1

Liposomes with an average diameter of 100 nm were formed by the lipid film hydration technique coupled with sequential extrusion. MPPC and DPPC were dissolved in a solution of $CHCl_3/EtOH$ (4:1 v/v). The solvent was gently removed under reduced pressure and a thin lipidic film was obtained. The lipidic film was hydrated in a solution of 50 mM $NH_4PF_6$ and 50 mM [Tm(hpdo3a)($H_2O$)] in 20 mM HEPES buffer at a pH of 7.4. The dispersion was extruded several times through polycarbonate membrane filters with pore diameters of 200 nm and 100 nm, subsequently. The obtained liposomes were dialysed overnight at 4° C. to remove $NH_4PF_6$ and [Tm(hpdo3a)($H_2O$)] that were not entrapped after hydration of the lipidic film. Dialysis was performed against a buffer with 20 mM HEPES buffer containing 0.3 M NaCl to obtain aspherical liposomes.

Reference is made to Table 1 for the composition of liposomes A-D.

TABLE 1

| Low-temperature-sensitive liposomes (LTSL). | | | | |
|---|---|---|---|---|
| Formulation | MPPC [mol %] | DPPC [mol %] | $NH_4PF_6$ [mM] | [Tm(hpdo3a)($H_2O$)] [mM] |
| A | 10 | 90 | 50 | — |
| B | 10 | 90 | 50 | 50 |
| C | 10 | 90 | 25 | 50 |
| D | 10 | 90 | 10 | 50 |

EXAMPLE 2

In a similar manner liposomes are prepared of different temperature sensitivity, viz. low (LTSL), traditional (TTSL) and non (NTSL) temperature sensitivity.

The compositions of these liposomes are indicated in Table 2.

TABLE 2

| Formulation | MPPC [mol %] | DPPC [mol %] | HSPC [mol %] | DPPE-PEG2000 [mol %] | DSPE-PEG2000 [mol %] | Cholesterol [mol %] |
|---|---|---|---|---|---|---|
| E (LTSL) | 9.7 | 86.5 | — | 3.8 | — | — |
| F (TTSL) | — | 53.7 | 27.0 | 3.2 | — | 16.1 |
| G (NTSL) | — | — | 58.7 | — | 2.3 | 39.0 |

The effects on CEST MRI as well as on $^{19}F$ MRI of the various formulations is measured with reference to the foregoing description of FIGS. 4-11.

The invention claimed is:

1. A carrier adapted for the localized delivery of a biologically active agent, comprising a shell capable of releasing an enclosed biologically active agent as a result of a local stimulus, wherein the shell encloses a 19F MR contrast agent and a 1H MR contrast agent in a cavity formed by the shell, wherein the 19F MR contrast agent undergoes a change in detectability and becomes detectable upon its release from the shell.

2. A carrier according to claim 1, wherein the 19F contrast agent is selected from the group consisting of the compounds of -continued X = B, C, N, O, P, P(O), P(O$_2$), P(O$_3$), S, S(O), S(O$_2$)
Z = CO$_2^-$, SO$_3^-$, PO$_3^{2-}$, OH
0 < (n, m, o) < 10
p = 0 or 1
q = 1, 2, 3, 4

3. A carrier according to claim 1, wherein the 1H MR contrast agent is selected from the group of T1 and/or T2 modifying contrast agents, Chemical Exchange-dependent Saturation Transfer (CEST) contrast agent, and combinations thereof.

4. A carrier according to claim 1, wherein the shell comprises a thermosensitive material capable of affecting drug release.

5. A carrier according to claim 1, wherein the shell is semipermeable, wherein the cavity further comprises a paramagnetic chemical shift reagent and a pool of proton analytes, and wherein the shell allows diffusion of the proton analytes.

6. A carrier according to claim 5, having a non-spherical shape.

7. A carrier according to claim 5, wherein the pool of proton analytes comprises water.

8. A carrier according to claim 1, being a thermosensitive nanoparticle selected from the group consisting of liposomes, polymersomes, nanocapsules, and mixtures thereof.

9. A carrier according to claim 1, comprising a metal complex having a metal ion and a ligand that is based on a multidentate chelate ligand, as a paramagnetic chemical shift reagent.

10. A carrier according to claim 9, wherein the metal complex has at least one coordination site of the metal left open for the coordination of at least one water molecule.

11. A carrier according to claim 10, wherein the paramagnetic shift reagent is selected from the group consisting of [Ln(hpdo3a)(H2O)], [Ln(dota)(H2O)]—, [Ln(dotma)H2O)]—, [Ln(dotam)(H2O)]3+, [Ln(dtpa)(H2O)]2-, derivatives thereof, and mixtures thereof, with Ln being a lanthanide ion.

12. A carrier according to claim 1 comprising a paramagnetic agent in or at its outer surface.

13. A carrier according to claim 12, wherein the paramagnetic agent is selected from the group consisting of at least one of the lanthanide ions Dy3+, Ho3+, Er3+, Tm3+, or Yb3+ complexed by a multidentate chelating molecule bearing at least one hydrophobic group that comprises at least 6 carbon atoms.

14. A carrier according to claim 1, comprising a drug in the treatment of cancer or cardiovascular disorders.

15. A carrier according to claim 1, comprising a ligand for targeted binding exposed on the outer surface of the carrier.

16. A carrier according to claim 15, wherein the ligand comprises a hydrophobic tail, the tail penetrating into a lipid bilayer shell of the carrier.

17. A carrier according to claim 15, wherein the ligand is a disease-specific molecular probe.

18. A method for the MRI guided delivery of a bio-active agent to a subject, comprising the administration to said subject of a carrier according to claim 1 provided with the bio-active agent, allowing the carrier to release the bio-active agent, and rendering a 19F MR image using the contrast provided by the 19F MR contrast agent.

19. A method according to claim 18, wherein the carrier comprises a CEST contrast agent, and wherein prior to and/or during release of the bioactive agent an MR image is rendered using the CEST contrast enhancement provided by said CEST contrast agent.

* * * * *